Figure 1:
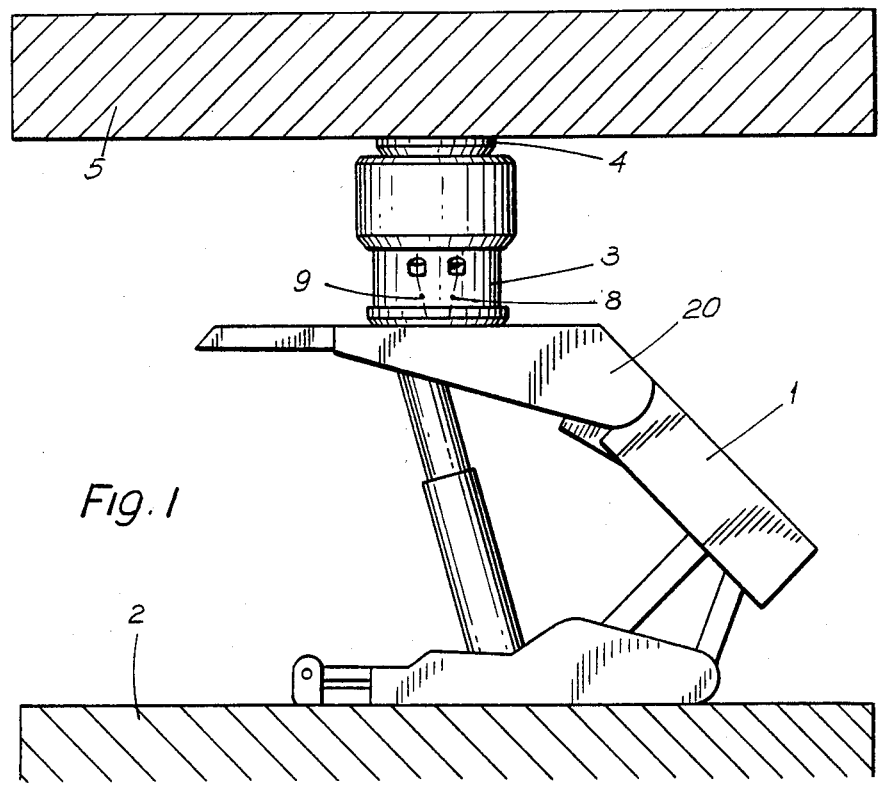

United States Patent [19]

Warachim et al.

[11] Patent Number: 4,718,793
[45] Date of Patent: Jan. 12, 1988

[54] GENERATOR FOR DYNAMIC LOADING OF A MINE LINING

[75] Inventors: Waclaw Warachim, Gliwice; Wojciech Skoczynski, Katowice; Jan Debiec; Hubert Niesyto, both of Gliwice; Marek Wojtaszczyk, Katowice; Edward Wlodarczyk, Warsaw; Roman Krzewinski, Warsaw; Mieczyslaw Zielinski, Warsaw; Kazimierz Kowalczyk, Kazun Nowy; Andrzej Spychala, Warsaw, all of Poland

[73] Assignees: Gwarectwo Mechanizacji Gornictwa "POLMAG"; Centrum Mechanizacji Gornictwa "KOMAG", both of Gliwice, Poland

[21] Appl. No.: 816,754

[22] Filed: Jan. 7, 1986

[30] Foreign Application Priority Data

Jan. 17, 1985 [PL] Poland .................................. 251575

[51] Int. Cl.⁴ .............................................. E21D 11/00
[52] U.S. Cl. ..................................... 405/303; 405/291; 405/294
[58] Field of Search ............... 405/291, 292, 293, 294, 405/295, 296, 297, 298, 299, 300, 301; 299/1, 13; 102/530, 531

[56] References Cited

U.S. PATENT DOCUMENTS

| | | | |
|---|---|---|---|
| 3,375,668 | 4/1968 | Allen | 405/293 |
| 3,732,725 | 5/1973 | Allen, Jr. et al. | 227/9 |
| 3,820,703 | 6/1974 | Rangger | 227/10 |
| 3,887,237 | 6/1975 | Bailey et al. | 299/13 |
| 4,025,029 | 5/1977 | Kotas et al. | 227/10 |
| 4,131,299 | 12/1978 | Ono et al. | 102/531 |
| 4,433,945 | 2/1984 | Irresberger | 405/290 |
| 4,498,391 | 2/1985 | Gergö et al. | 299/13 |

Primary Examiner—Dennis L. Taylor
Attorney, Agent, or Firm—Ladas & Parry

[57] ABSTRACT

A generator for dynamic loading of a mine lining simulates an unstable ground structure, such as a "bump" of the formation roof by an explosion of an explosive. The generator /3/ comprises a cylinder /6/ with a piston /7/, the said piston functioning as a percussion member. The bottom of the cylinder /6/ is provided with symmetrical chambers /10/ to place an explosive. The explosive is batched to each of chambers /10/ through holes /8, 9/ made in the flank of the cylinder /6/. Holes /8, 9/ are bored at an angle enabling gravitational filling of the chamber /10/ with an explosive already after initial spragging of the lining section /1/ under test between the floor /2/ and the generator /3/ abutting the roof /5/ of the test-stand. The cylinder /6/ is closed with a limiter /12/ of the stroke of the piston. Between the piston /7/ and the limiter /12/ of its stroke there is a shock-absorbing washer /13/. In the limiter /12/ there are additional holes for release of powder gases.

4 Claims, 2 Drawing Figures

GENERATOR FOR DYNAMIC LOADING OF A MINE LINING

The subject of the invention is a generator for dynamic loading of a mine lining appropriated for supporting the roof of a heading in an unstable ground structure. The quality of the design of the mine lining appropriated for application in a particular ground structure is tested at a test-stand simulating dynamic load of the lining.

The known test-stands with simulation of dynamic loads are adapted to testing only hydraulic props being the main supporting member of a section of a mine lining. They are units of a pile-driver type, in which energy released by the prop has a harmful effect on the base, causing vibration of soil. Vibration transferred by the base causes damages of buildings and is even a hazard to the surrounding natural environment.

Those skilled in the art know from the Polish patent application No. 232584 published in No. 4/84 of the Patent Office Bulletin of Feb. 14, 1983, a unit for dynamic tests of structural members, especially servomotors of mechanized wall linings. In the said unit dynamic load is brought about by an explosive, and the design of the said unit hinders transfer of the load to the environment. A pressure pulse generator included in the unit comprises a cylindrical body closed at one side with a bottom and a piston as a percussion member. Inside the cylindrical body there is an explosive and a primer. The explosive is put into the cylinder body outside the test unit, and thereafter by means of a crane unit the said cylinder is carried into the test unit and is closed with the piston. The hydraulic servo-motor under test abuts the piston. The cylinder and the servo-motor under test, placed along a common axis, are limited by two plates parallel to each other, being the equivalents of the floor and the roof of the mine heading. After detonation of the explosive inside the cylindrical body, the hydraulic servo-motor under test gets destroyed. Indicators, with which the unit is equipped, record certain parameters of the hydraulic servo-motor, which change in the result of the said destruction simulating an unstable ground structure such as a "bump" of the formation roof. A "bump" is a sudden shock or rock concussion sometimes accompanying rock subsidence in and around mines.

A disadvantage of the known pressure pulse generator is that before any subsequent test of parameters of the servo-motor it is necessary to disassemble the generator in order to place an explosive and to mount it again in the test unit.

The object of the invention is a dynamic load generator in which it is possible to detonate an explosive many times without the necessity of dismounting and then mounting again the cylinder each time, and what, in consequence, enables carrying out subsequent tests in the identical position of the generator and the element under test in relation to each other.

The essence of the solution according to the invention consists in that the generator has a cylinder with chambers in the bottom thereof to place an explosive. The flank of the cylinder is provided with two holes in the direction of one of the said chambers. The holes bored in the flank of the cylinder enable gravitational filling up the chamber with an explosive already after initial spragging of the lining section under test between the floor and the generator abutting the roof of the test-stand. Spragging is the act of propping a mine with a piece of timber or other prop. The cylinder is closed with a piston stroke limiter fixed on the edge of the said cylinder. Between the piston and the limiter of its stroke there is a shock-absorbing washer. Besides, the stroke limiter is provided with holes for release of powder gases.

In a version of the generator according to the invention the flank of its cylinder is provided with two holes aslant to the second chamber.

The design of the generator according to the invention enables multiple loading of the lining section under test at one initial spragging thereof and causing bigger and bigger dynamic load until a damage of the lining section under test. Due to this it is possible to apply the generator for testing sections of the lining not only at a test-stand but also in an underground heading where, from the vary nature of things, there is no room for the mentioned crane unit.

Figure 2:
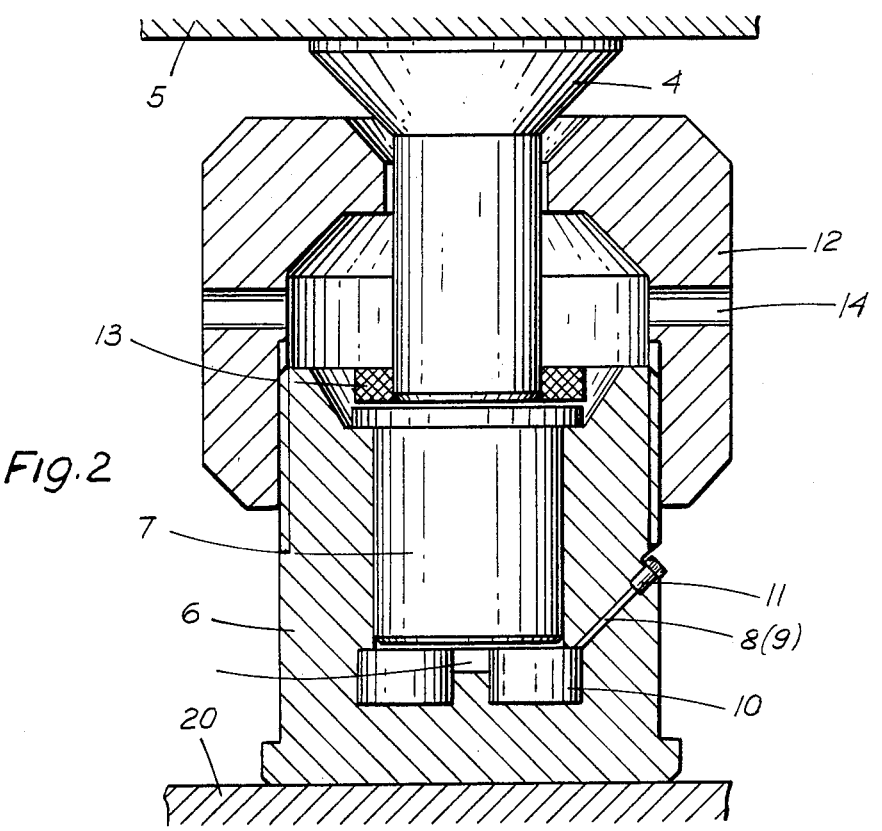

The subject of the invention in an exemplary embodiment is shown in a drawing, in which FIG. 1 presents a generator built in at a test-stand between the roof supporting beam of the lining section under test and the roof, and FIG. 2 presents the vertical section of the generator.

A lining section 1 under test is set on the floor 2 of a test-stand. The lining section 1 has a roof supporting beam 20. A generator 3 of dynamic loading is built in, which through a connector 4 of the generator abuts the roof 5 of the stand. The lining section 1 under test gets spragged between the floor 2 and the generator 3 abutting the roof 5 to the value of support pressure.

The generator 3 for dynamic loading of the lining comprises a cylinder 6 whose bottom abuts the roof supporting beam 20 of the lining section 1 being tested. Inside the cylinder 6 there is a piston 7 which through a connector 4 abuts the roof 5 of the test-stand. The force of initial spragging of the lining section 1 under test is transferred through the cylinder 6, the piston 7 and the connector 4 to the roof 5 of the test-stand. In the flank of the cylinder 6 there are two angled or slanting holes 8 and 9 one of which serves for putting in an explosive to one of explosion chambers 10 in the bottom of the cylinder 6, and the other hole serves for putting in a primer. Holes 8 and 9 are plugged with threaded plugs 11.

Detonation of an explosive in the chamber 10 is effected with a shooting equipment. During the explosion the piston 7 is projected from the cylinder 6 by pressure of shooting gases, which causes loading of the lining section 1 with a dynamic force exceeding the force of initial spragging thereof. In the case of destroying the lining section under test during the explosion the piston 7 cannot leave the cylinder 6 which is closed by a collar or limiter 12 for limiting the stroke. A washer 13 of a soft material, situated between the piston 7 and the limiter 12 of the stroke, limits percussions of the piston 7 against the limiter 12. Powder gases escape through a gap between the cylinder 6 and the piston 7, and additionally also through holes 14 made in the limiter 12.

In order to compensate loads of the piston during detonation of an explosive, chambers 10 in the bottom of the cylinder 6 are arranged symmetrically and are connected among themselves by a passage 15. In a version of an embodiment of the generator to the second chamber 10 two slant holes 8 and 9 lead as well. In the case of a misfire in one of the chambers 10 filled with an explosive, an additional detonator is screwed in to the second chamber 10, a small amount of an initiating material is poured in, and an explosion is initiated again.

What is claimed is:

1. Apparatus for dynamically testing a section of mine lining comprising:

a mine lining section spragged between a lower supporting surface and an upper support;

a bump simulating means connected between said mine lining section and said upper support, said pump simulating means comprising:

a cylinder;

a piston disposed within said cylinder;

a collar encompassing said cylinder and said piston for limiting the stroke of said piston;

a chamber in the bottom of said cylinder for an explosive charge;

a port in said cylinder wall for supplying explosive to said chamber, whereby said bump simulating means can be recharged in situ.

2. The apparatus of claim 1 wherein a shock-absorbing washer is disposed between the piston and said collar.

3. Apparatus of claim 1 wherein said collar has passages permitting exhaust gases to escape from said chamber.

4. Apparatus of claim 1 wherein said chamber comprises two interconnected chambers, each chamber having a separate port.

* * * * *